(12) United States Patent
Thornton et al.

(10) Patent No.: US 6,765,042 B1
(45) Date of Patent: Jul. 20, 2004

(54) ACIDIC SUPERABSORBENT POLYSACCHARIDES

(75) Inventors: Jeffrey Wilson Thornton, Huizen (NL); Bas Schraven, Nijmegen (NL); Harm Jan Thiewes, Woudenberg (NL); Dorine Lisa Van Brussel-Verreast, Bodegraven (NL); Luca Bemporad, Gothenburg (SE); Anne-Mieke Yvonne Wilhelmina Verwiiligen, Zeist (NL); Arie Cornelis Besemer, Amerongen (NL); Pia Kalentuin, Torslanda (SE)

(73) Assignee: SCA Hygiene Products Zeist B.V., Zeist (NL)

( * ) Notice: Subject to any disclaimer, the term of this patent is extended or adjusted under 35 U.S.C. 154(b) by 0 days.

(21) Appl. No.: 09/868,139

(22) PCT Filed: Dec. 16, 1999

(86) PCT No.: PCT/NL99/00776

§ 371 (c)(1), (2), (4) Date: Sep. 19, 2001

(87) PCT Pub. No.: WO00/35504

PCT Pub. Date: Jun. 22, 2000

(30) Foreign Application Priority Data

Dec. 16, 1998 (EP) .............................. 98204273
Apr. 23, 1999 (EP) .............................. 99201286
Jun. 15, 1999 (EP) .............................. 99201915

(51) Int. Cl.⁷ .............................. C08J 3/24; C08J 3/12; C08G 65/04; C08F 8/00
(52) U.S. Cl. .............................. 523/400; 524/387; 526/903; 527/300; 528/421; 528/486; 528/491; 528/503
(58) Field of Search .............................. 523/400; 524/387; 525/385; 526/903; 528/421, 486, 491, 503

(56) References Cited

U.S. PATENT DOCUMENTS 3,901,236 A * 8/1975 Assarsson et al.
4,371,208 A    2/1983 Sticker
4,582,865 A    4/1986 Balazas et al.
4,657,080 A *  4/1987 Hodge
4,755,468 A    7/1988 Jung et al.
4,963,666 A * 10/1990 Mälson
5,247,072 A    9/1993 Ning et al.
5,371,208 A   12/1994 Kozulic
5,452,232 A    9/1995 Espinoza et al.
6,331,619 B1 * 12/2001 Besemer et al.

FOREIGN PATENT DOCUMENTS

EP    202127    11/1986
EP    644207     3/1995
EP    889063     7/1997
WO   97/28298    8/1997
WO   98/27117    6/1998
WO   99/29354    6/1999

OTHER PUBLICATIONS

Rutenberg, M.W., et al., "Starch Derivatives: Production and Uses", Acad. Press Inc., 1984, pp 324–332.

Coviello, T., et al., "A Novel Co–Crosslinked Polysaccharide: Studies for a Controlled Delivery Matrix", Journal of Controlled Release, vol. 55, No. 1, Oct. 30, 1998, pp 77–66.

* cited by examiner

*Primary Examiner*—Tae H Yoon
(74) *Attorney, Agent, or Firm*—Burns, Doane, Swecker & Mathis, L.L.P.

(57) ABSTRACT

A process is disclosed for producing an acidic superabsorbent polysaccharide derivative, comprising the steps of: (a) crosslinking at least one polysaccharide containing acidic groups, such as carboxymethyl cellulose and/or 6-carboxy starch, with a crosslinking agent to produce a gel; (b) if necessary, adjusting the pH of the polysaccharide to a value between 3.5 and 5.5; (c) comminuting the acidified polysaccharide gel; and (d) drying the comminuted polysaccharide at elevated temperature. The superabsorbent polysaccharide obtainable by this process has a pH below 5 and provides odour control when contacted with malodorous fluids.

17 Claims, No Drawings

ACIDIC SUPERABSORBENT POLYSACCHARIDES

This application is a § 371 national stage application of International Application No. PCT/NL99/00776, filed Dec. 16, 1999, which claims priority to EP Application No. 98204273.1, filed Dec. 16, 1998, EP Application No. 99201286.4, filed Apr. 23, 1999, and EP Application No. 99201915.8, filed Jun. 15, 1999, each of which are hereby incorporated by reference in their entirety.

The present invention relates to a superabsorbent material which has enhanced odour control and prevents bacterial growth, based on polysaccharides, and to a method of producing such material.

Superabsorbent materials of various types are known in the art. Examples are crosslinked polyacrylates and polysaccharides grafted with polyacrylates. A problem related to the use of superabsorbent materials is the odour caused by urine components which cause superabsorbent materials to become objectionable long before their maximum absorbing capacity has been used. Furthermore, the known absorbent materials are normally based on non-renewable and/or non-biodegradable raw materials. Consequently, there is a need for superabsorbent materials, which have odour control and reduced bacterial growth when contacted with body fluids, and which are biodegradable.

WO 98/27117 discloses a superabsorbent polysaccharide derivative obtained by oxidation and crosslinking of a polysaccharide such as starch, in which at least 0.1 carbinol group per monosaccharide unit of the polysaccharide derivative has been oxidised to a carboxyl group, the total number of carboxyl groups per monosaccharide unit being 0.2–3.0, and the derivative results from reaction with at least 0.001 equivalent of crosslinking agent per monosaccharide unit. The derivatives are not devised for odour control. U.S. Pat. No. 5,247,072 describes superabsorbent carboxyalkyl polysaccharides, especially carboxymethyl cellulose, without odour control, obtained by crosslinking as a result of heat treatment. EP-A-202127 discloses superabsorbent articles for reducing diaper rash, which contain acid in distinct zones to control the skin pH between 3.0 and 5.5.

It has been found that a superabsorbent polymer with improved odour control can be produced by a process comprising the steps of:

(a) crosslinking at least one polysaccharide containing acidic groups with a crosslinking agent to produce a gel;

(b) ensuring that pH of the polysaccharide is between 3.5 and 5.5 and, if necessary, adjusting the pH to between 3.5 and 5.5, especially to between 3.9 and 4.9;

(c) comminuting the acidified polysaccharide gel; and (d) drying the comminuted polysaccharide at elevated temperature.

The term "polysaccharide containing acidic groups" is understood to comprise polysaccharides having a pK ot less than 5, down to about 1.5. Such polysaccharides may contain carboxylic groups, sulphonic groups (—(O)—$SO_2$—OH), phosphonic groups (—(O)—$PO(OH)_2$), ammonium groups (—$NR_2H^+$, wherein R is alkyl or hydrogen) and combinations thereof. The carboxylic groups may be present as a result of carboxyalkylation, in particular carboxymethylation, or as a result of reaction with an anhydride such as maleic or succinic anhydride or as a result of oxidation, e.g. of a hydroxymethyl group (—$CH_2OH$, usually at C6 of a monosaccharide unit), or of a bis (hydroxymethylene) group (—CHOH—CHOH—, usually at C2–C3 of a monosaccharide unit).

The phosphonic groups may be present as phosphate groups, resulting e.g. from reaction with phosphorylating agents (see e.g. WO 97/28298), or as phosphonic or phosphinic acid groups, resulting e.g. from reaction with haloethyl phosphonic acids. The sulphonic acids may be present e.g as sulphate groups or as a result of sulphite addition to polysaccharide aldehydes (see e.g. WO 99/29354) or to maleic anhydride adducts (products with —O—CO—CH—CH(COOH)—$SO_3H$ groups). The ammonium groups are also acidic groups, and can result from protonation of amine groups, such as in chitosan-type polysaccharides or in aminoalkylated polysaccharides.

The polysaccharides may be α-glucans like starch, amylose and amylopectin, β-glucans like cellulose and chitin and scleroglucan, galactomannans like guar gum (guaran) and locust bean gum, glucomannans including e.g. xanthan gum, fructans, (arabino)xylans, galactans including alginates and pectin and other mixed polysaccharides. Starch and cellulose are particularly preferred. Starch may be derived from any suitable source, such as corn, wheat, potato, rice and the like; it may also be a residual, crude or lower-grade starch product containing minor amounts of other biopolymers such as cellulose, pectin or protein. Cellulose may also contain minor amounts of other materials such as hemicellulose.

The polysaccharides may comprise non-ionic, non-carboxylated derivatives such as hydroxyalkyl polysaccharides, but the presence of such non-ionic derivatives does not have a particular advantage. The chain length of the polysaccharides is important although there is no critical minimum for the molecular weight. In general, polysaccharides having a molecular weight of more than 1,000 are preferred. A molecular weight above about 25,000 may have a positive effect on the properties of the oxidised product.

The acidic polysaccharide can be a carboxymethyl polysaccharide without further substitution, such as carboxymethyl cellulose, preferably having a degree of substitution of 0.3–3.0, more preferably 0.5–1.5. For such carboxymethylated polysaccharides, the process advantageously comprises the further step of contacting the crosslinked polysaccharide with an organic solvent which is at least partly miscible with water, between step (b) and step (c). The organic solvent is preferably a water-miscible alcohol such as methanol, ethanol, methoxyethanol or isopropanol, a water-miscible ether such as dioxane, tetrahydrofuran or dimethoxyethane, or a water-miscible ketone, such as acetone. Most preferred are methanol and ethanol. The amount of solvent can be e.g. 2–30 times the amount of the gelled polysaccharide. The water-miscible solvent is evaporated before or during step (d).

The carboxymethylated polysaccharide can also be a carboxymethyl polysaccharide containing further carboxyl groups produced by oxidation of saccharide carbinol groups. Such carboxyl groups may be 2- and/or 3-carboxyl groups obtained by oxidation of anhydroglycose rings of the polysaccharide using hypochlorite or periodate/chlorite, but preferably they are 6-carboxyl groups obtained by oxidation of the 6-hydroxymethyl group, e.g. with a nitroxyl compound (TEMPO) as a catalyst. In such carboxy-carboxymethyl polysaccharide, such as 6-carboxy-carboxymethyl starch or 6-carboxy-carboxymethyl-cellulose, the degree of substitution for carboxymethyl is preferably 0.2–0.8, especially 0.3–0.6, and the degree of substitution for (6-carboxyl groups is preferably 0.1–0.5, more preferably 0.15–0.4.

Suitable oxidation methods are described in WO 98/27117 and references cited therein. TEMPO oxidation may be performed with hypochlorite with or without bromide as a catalyst, or with peracid/bromide or another oxidant. Unsubstituted TEMPO or 4-hydroxy or 4-acetamido-TEMPO or mixtures thereof may be used. When oxidations resulting in salt production are used, the salts may advantageously be removed after the oxidation reaction.

Similarly, the acidic polysaccharide may contain both other acidic groups obtained by substitution, and carboxyl groups obtained by oxidation. Such other acidic groups obtained by oxidation include e.g. phosphonic groups obtained by phosphorylation of the polysaccharide, sulphonyl groups and carboxyalkylcarbonyl groups obtained by reaction with a dicarboxylic anhydride. Substitution and oxidation may be performed in either order, e.g. first phosphorylation and then oxidation, or first oxidation and then phosphorylation. Combinations of different acidic substituents e.g. carboxylalkyl groups and phosphonic groups are also suitable.

In such oxidised and subsituted (carboxyalkyl or other) polysaccharides the addition of an organic water-miscible solvent can be dispensed with, as a gel with the required structure already results from direct cross-linking.

The polysaccharide containing acidic groups can also be a carboxylated polysaccharide wherein the carboxyl groups have been introduced by oxidation of saccharide carbinol groups in a manner as described above, without carboxyalkylation. Such oxidised polysaccharides include dicarboxy polysaccharides (obtained by C2–C3 oxidation) and, especially 6-carboxy polysaccharides, e.g. obtained by TEMPO oxidation, especially 6-carboxy starch. These polysaccharides do not require the use of a water-miscible solvent after crosslinking.

The polysaccharide containing acidic groups may also be a mixture of acidic polysaccharides as described above. A particularly useful mixture is a mixture of carboxymethyl cellulose and 6-carboxy starch, e.g. in a ratio of between 1:1 and 1:20. Other mixtures are also quite useful, e.g. carboxymethyl cellulose and carboxymethyl starch, or carboxymethyl starch and cellulose phosphate having a degree of substitution of about 0.3 to about 0.5.

The polysaccharide containing acidic groups is reacted with a crosslinking agent to produce a gel. A gel is defined herein as a polymeric network based on polysaccharides, which swells in water and does not dissolve in water. Crosslinking agents are reagents containing two or more functions capable of reacting with a hydroxyl group, resulting in intra- and inter-molecular bonds between different mono-saccharide units. Suitable cross-linking agents may act on the hydroxyl groups of different polysaccharide chains and include divinyl sulphone, epichlorohydrin, diepoxybutane, diglycidyl ethers, diisocyanates, cyanuric chloride, trimetaphosphates, phosphoryl chloride, and mixed anhydrides, and also inorganic crosslinkers such as aluminium and zirconium ions, but are not restricted to these examples. Mixtures of crosslinkers may also be used.

Especially preferred crosslinkers, in particular for crosslinking at elevated temperature and/or concentration, are crosslinkers that are active under neutral or acidic conditions, such as bis-epoxy crosslinkers, for example diepoxybutane, 1,5-diepoxyhexane, 1,7-diepoxyoctane, bis-glycidyl ether, glycol bis-glycidyl ether, butanediol bis-glycidyl ether and the like, as well as mixtures of different crosslinkers. Crosslinking can also be performed using carboxyl or aldehyde groups formed by oxidation or carboxyl groups introduced by carboxyalkylation, e.g. using polyols, polyamines or other polyfunctional reagents. Esterification and other crosslinking methods described herein can also he effected intramolecularly at the surface between the carboxyl group of one polysaccharide chain and a hydroxyl group of another chain as known in the art. This inter-chain crosslinking can be catalysed by an acid or a multivalent ion such as magnesium or calcium, or by heating. Divinyl sulphone is another preferred crosslinker. Crosslinking of starch and other polysaccharides is well-known in the art. A description of crosslinking agents and reaction conditions can be found e.g. in "*Starch Derivatives: Production and Uses*" by M. W. Rutenberg and D. Solarek, Acad. Press Inc., 1984, pages 324–332.

According to a preferred embodiment of the invention, crosslinking is performed under conditions of increased temperatures and high concentrations. The temperatures are typically at least 100° C. more preferably between 120 and 180° C. The concentration of the polysaccharide to be crosslinked is at least 20% by weight, more particularly between 25 and 65% by weight with respect to the total aqueous crosslinking mixture. The crosslinking mixture may further contain a plasticiser such as a polyol. Suitable polyol plasticisers include glycerol, ethylene glycol, propylene glycol, polyethylene glycol, polypropylene glycol, glycol and glycerol monoesters, sorbitol, mannitol, monosaccharides, citric acid monoesters and the like. The amount of plasticiser may vary from 1 to 25% weight of the crosslinking mixture. The crosslinking can be conveniently performed in a kneading apparatus or an extruder under conditions of reactive processing. The various components of the crosslinking mixture can be mixed before entering the extruder, or one or more of them, e.g. the crosslinking agent, may be added at a later stage in the extruder.

After crosslinking, the crosslinked polysaccharide is treated with an acid so as to reduce the pH to 3.5 to 5.5. However, if the crosslinking is performed under acidic conditions, such as with bis-epoxy crosslinkers, the acidification takes place before cross-linking, and an adjustment of a pH to between 3.5 and 5.5 may or may not be needed after the crosslinking step. Suitable acidifying reagents include inorganic and organic acids such as hydrochloric, phosphoric, acetic acid etc. If crosslinking is performed under normal conditions (ambient temperature or up to about 100° C., atmospheric pressure, lower concentration) or before acidification, it is preferred that the polysaccharide is acidified to pH 4.9 or lower. After acidification, the cross-linked, gel-like material is comminuted to smaller particles, e.g. in the range of 0.5–5 mm.

Instead of or in addition to the treatment with the water-miscible organic solvent described above, an additional post-crosslinking step (surface crosslinking) may be applied to strengthen the gel. This post-crosslinking may be performed after the comminuting step c or even after the drying step d, resulting in different swelling degrees of the gel particles obtained. The crosslinking agent to be used in this post-crosslinking step can be the same as those referred to above for the first crosslinking step. In this procedure, the gel particles are slightly swollen, and treated and mixed with a crosslinking agent, and subsequently the particles are dried at a temperature which depends on the liquid used to swell the gel particles and on the crosslinking agent. The post-crosslinking may be performed in the presence of compounds providing further crosslinks at the outside of the gel particle. Such compounds may include bifunctional or multifunctional capable of reacting with hydroxyl and (if still present) carboxyl functions, for example diamines, polyamines, polyamide-amine-epichlorohydrin (PAE resin), bis-epoxy compounds, chitosan-like compounds, metal salts (zirconium, aluminium), dialdehydes, or polyaldehyde-polycarboxy starch derivatives.

The comminuted material is dried, preferably in a fluidised bed drier. Drying can be performed at ambient temperatures, but preferably increased temperatures are used, in a particular above 50° C., more in particular above 70° C. Drying times from 15 minutes up to 8 hours or more can be applied. Preferably an additional heat treatment is performed after the initial (fluidised bed) drying; this additional drying step can be performed at 80–150° C. e.g. for 2 minutes to 2 hours, and results in a further enhanced gel strength of the product.

The invention also pertains to a bacteriologically stable superabsorbent polysaccharide derivative having odour control of absorbed liquid, as well as to a superabsorbent article in which this derivative is incorporated. The derivative and the article preferably have a pH below 5 (down to 3.5) when contacted with neutral or near-neutral water; if necessary, an acidifying agent can be incorporated in a sufficient amount to maintain the required low pH. Suitable acidifying agents include organic di- or poly-carboxylic acids such as citric, maleic, fumaric, oxalic, malonic, succinic, tartaric and similar acids, hydroxyacids such as gluconic, ascorbic, glycolic, glyceric, lactic, malic, salicylic acid and the like, as well as benzoic acid and phosphoric and other inorganic acids. These acids may be used in combination with their partially neutralised salts (e.g. monosodium citrate or monopotassium phosphate) to provide buffering capacity. Also, neutral materials such as acid anhydrides and lactones, e.g. maleic anhydride, succinic anhydride, δ-gluconolactone, can be incorporated for lowering the pH.

The superabsorbent polysaccharides combine high absorption capacity with control of bacterial growth and control of odour, as well as with biodegradability. The absorption capacity can be expressed as free swelling capacity (FSC) and the centrifugal retention capacity (CRC), and with the absorption under load (AUL), using synthetic urine (SU) as lest liquid. The composition of the synthetic urine is as follows: 300 mM urea, 60 mM KCl, 130 mM NaCl, 2.0 mM $CaSO_4 \cdot 2H_2O$, 3.5 mM $MgSO_4$, and 1 mg/l Triton X-100 in deionised water.

The superabsorbent polysaccharide derivatives of the invention can be used for ot absorbing liquids, especially of body fluids which contain various salts and non-ionic substances. The product is particularly suitable for the production of absorbent hygiene articles, such as diapers, sanitary napkins and the like. Such articles can be produced entirely on the basis of the polysaccharides according to the invention, but they can also contain conventional absorbent materials, such as cellulose pulp in addition to the absorbents according to the invention. The absorbent article is preferably part of a layered product, in which the superabsorbent polymer constitutes at least one layer. The absorbent layer can be located between a liquid-pervious top layer and a liquid-impervious bottom layer. In particular the product may have four layers. The first one can be a thin, non-woven layer of polyester fibres or other fibres. The second layer can be a wadding which is used for acquiring and spreading the absorbed fluid such as urine. The third layer can consist of fluff pulp wherein the SAP is spread as fine particles, especially 50–800 μm. The last layer can be a back sheet of a water-resistant material such as polyethylene, which prevents leakage from the layered absorption product.

EXAMPLE 1

Absorbent 6-carboxy-carboxymethyl Potato Starch

Carboxymethyl starch (degree of substitution 0.5) derived from potato starch was converted to 6-carboxy carboxymethyl starch by TEMPO-catalysed oxidation (degree of oxidation 0.25). A 20% aqueous solution of the product was cross-linked with different amounts of divinyl sulphone (0.5, 0.6, 0.7 mol % DVS). After 15 hours, an insoluble network was formed. The gel was brought into distilled water and allowed to swell. The pH of the material was lowered to pH 4.1 by controlled addition of 1 M HCl. After equilibration, the gel was filtrated and dried in a fluidised bed drier at 70° C. The following absorption characteristics (FSC, CRC, AUL at 2.0 kPa) measured in synthetic urine (SU) were obtained:

| Cross-linking degree (mol % DVS) | FSC (g/g) | CRC (g/g) | AUL (g/g) 2 kPa | pH gel |
|---|---|---|---|---|
| 0.5 | 31 | 19 | 12 | 4.1 |
| 0.6 | 30 | 18 | 14 | 4.1 |
| 0.7 | 27.5 | 17 | 18.5 | 4.1 |

EXAMPLE 2

Absorbent 6-carboxy-carboxymethyl High Amylose Corn Starch

Carboxymethyl starch (degree of substitution 0.53) derived from high amylose corn starch was converted to 6-carboxy carboxymethyl starch by TEMPO-catalysed oxidation (degree of oxidation 0 09). A 20% aqueous solution of the product was cross-linked with different amounts of divinyl sulphone (1.0, 1.5, 2.0, 2.5 mol % DVS). After 16 hours, an insoluble network was formed. The gel was brought into distilled water and allowed to swell. The pH of the material was lowered to about pH 4.1 by controlled addition of 1 M HCl. After equilibration, the gel was filtrated and dried in a fluidised bed drier at 80° C. The above table summarises the absorption characteristics (FSC, CRC, AUL) measured in synthetic urine (SU) as obtained.

| Cross-linking degree (mol % DVS) | FSC (g/g) | CRC (g/g) | AUL (g/g) 2 kPa | pH gel |
|---|---|---|---|---|
| 1.0 | 29.5 | 20 | 17 | 4.0 |
| 1.5 | 34.5 | 20.5 | 13 | 4.1 |
| 2.0 | 33.0 | 18 | 16 | 4.3 |
| 2.5 | 28.5 | 16 | 17 | 4.0 |

EXAMPLE 3

Absorbent Carboxymethyl Cellulose Treated with Methanol

| DXL[1] | XL reaction[2] cond. (° C./h) | FBD (° C./min) | FSC (g/g) | CRC (g/g) | AUL (g/g) |
|---|---|---|---|---|---|
| 10 | 20°/20 h[3] | 100°/10 m | 29 | 11 | 17 |
| 10 | 20°/20 h | 100°/10 m | 34 | 16 | 22 |
| 10 | 80°/3 h | 100°/10 m | 38 | 18 | 20 |
| 20 | 50°/8 h | 100°/10 m | 19.5 | 6.5 | 14 |
| 10 | 50°/8 h | 100°/10 m | 28.5 | 12 | 19.5 |
| 5 | 50°/8 h | 100°/10 m | 31.5 | 15 | 20.5 |

-continued

| DXL[1] | XL reaction[2] cond. (° C./h) | FBD (° C./min) | FSC (g/g) | CRC (g/g) | AUL (g/g) |
|---|---|---|---|---|---|
| 5 | 50°/15 h | 100°/15 m | 34.5 | 18 | 23 |
| 5 | 50°/15 h | 80°/15 m | 40 | 19.5 | 21 |
| 5 | 50°/15 h | 60°/15 m | 34 | 15.5 | 20 |
| 5 | 50°/15 h | 40°/30 m | 33 | 15 | 18.5 |

[1]: degree of crosslinking used, (mol % BDDE)
[2]: crosslinking reaction
[3]: pH controlled by acetic acid instead of HCl.

A 2 wt. % aqueous solution of CMC (Cekol 50,000 from Metsa Specialty Chemicals, degree of substitution 0.8) was prepared and the pH was adjusted to 4.0 by slow addition of HCl under stirring (alternatively, glacial acetic acid can be used according to WO 86/00912, example 2b). The required amount of a 10 or 20 vol. % aqueous solution of 1,4-butanediol diglycidyl ether (BDDE) was added and the reaction mixture was thoroughly mixed. The gel obtained was cut into pieces and suspended overnight in a fivefold excess of methanol. The methanol was filtered out and the gel was milled in a blender, and the particles were dried in a fluidised bed drier (FBD). The dried product was ground in a mortar. The absorption characteristics for synthetic urine (SU) are summarised in the table above with details on crosslinking and drying.

EXAMPLE 4

Absorbent Carboxymethyl Cellulose Treated with Methanol

A 2 wt. % solution of CMC (Cekol 50,000 from Metsa Specialty Chemicals, degree of substitution 0.8) in 0.05 M aqueous NaOH was reacted with 14 mol % of DVS for 18 hours at room temperature. The gel obtained was chopped in pieces of roughly 3–4 cm and the pieces were brought in a fivefold excess ot methanol. The gel was then acidified using 1M HCl to a pH varying from 4.4 to 4.0. After about 24 h the swollen gel was milled in a blender to obtain smaller particles, and then put back in the methanol for another 24 h to achieve homogeneous acidification of the gel material. Thereafter ground particles were dried in a fluidised bed drier at 100° C. for 30 min, and then further heat-treated at 120° C. in an oven for about 30 min. The absorption characteristics for SU are summarised in the following table.

| amount of acid added (ml) | pH gel | before thermal treatment | | | After thermal treatment | | |
|---|---|---|---|---|---|---|---|
| | | FSC (g/g) | CRC (g/g) | AUL (g/g) | FSC (g/g) | CRC (g/g) | AUL (g/g) |
| 28 | 4.4 | 83 | 64 | 10 | 40 | 26 | 17 |
| 30 | 4.2 | 57 | 42 | 12 | 29 | 17 | 16.5 |
| 33 | 4.0 | 55 | 41 | 13 | 28 | 15 | 16 |
| 35 | 4.0 | 39 | 26 | 13 | 21 | 11 | 15 |

EXAMPLE 5

Absorbent Carboxymethyl Cellulose Treated with Ethanol

Ten grams of CMC (Cekol 50,000) were dissolved in 500 ml NaOH (0.05 mol/l). At room temperature 0.62 ml DVS (14 mol %) was added under stirring. After 18 hours the crosslinked gel (450 g) was chopped into pieces and 28 ml of 1 mol/l HCl was added and thoroughly mixed to decrease the pH of the gel to 4.4. After 1 h 1400 ml of ethanol was added. After one week, the precipitated gel was ground with a blender and dried in an FBD for 30 minutes at 100° C. The dry particles were milled and sieved to obtain a final particle size of 100–800 μm. The following absorption characteristics (FSC, CRC, AUL) measured in synthetic urine were obtained: FSC: 132 g/g; CRC: 111 g/g; AUL: 11 g/g; pH gel 4.4.

EXAMPLE 5a

Absorbent Carboxymethyl Cellulose Treated with Ethanol

In addition to the sample of example 5, a heat treatment was applied for 30 minutes at 120° C. in an oven to improve the gel strength (AUL). The following absorption characteristics measured in synthetic urine were obtained: FSC: 52 g/g; CRC: 37 g/g; AUL: 17 g/g; pH gel 4.5.

EXAMPLE 6

Absorbent Carboxymethyl Cellulose Treated with Ethanol

Ten grams of CMC (Cekol 50,000, DS 0.8) were dissolved in 500 ml water and 8.5 ml 1 mol/l HCl (pH 4.4). Then 1.27 ml of 20% (v/v) BDDE in water (3 mol %) was added with stirring. After 8 hours at 50° C, the crosslinked gel was suspended in a threefold volume of ethanol with stirring. After one week, the precipitated gel was ground into small pieces with a blender and dried in a FBD for 15 minutes at 100° C. The dry particles were milled and sieved to obtain a final particle size of 100–800 μm. The following absorption characteristics measured in synthetic urine were obtained: FSC: 21 g/g; CRC: 13 g/g; AUL: 18 g/g; pH gel 4.3.

EXAMPLE 7

Absorbent 6-carboxy Starch/CMC Crosslinked Under Alkaline Conditions

Five g of TEMPO-oxidised starch (TOS, degree of oxidation 0.70) and 0.4 g of CMC (Cekol 50,000 from Metsa Specialty Chemicals, degree of substitution 0.8) were dissolved in 20 ml of 0.05 M aqueous NaOH (pH 12) under mechanical stirring for 4 h. The mixture was crosslinked with 0.8 mol % of DVS (23 μl) at 5° C. for 18 hours. Three g of the gel obtained was chopped in pieces and the pieces were brought in 600 ml of demi water and acidified with 1.8 ml of 1 M HCl with mild stirring (stepwise addition of acid). The next day, the swollen gel was filtered over a 80 μm sieve, and brought in another 600 ml of demi water for half an hour. Subsequently the gel was dried in a fluidised bed drier at 80° C. for 1 hour. The material was characterised in synthetic urine with the following results: 93% TOS/7% CMC: FSC: 30 g/g. CRC: 17 g/g, AUL: 16.5 g/g, pH gel 4.6.

EXAMPLE 8

Absorbent 6-carboxy Starch/CMC Crosslinked Under Acidic Conditions

Five g of TEMPO-oxidised starch (TOS, degree of oxidation 0.70) and 0.4 g of CMC (Cekol 50,000 from Metsa Specialty Chemicals, degree of substitution 0.8) were dissolved in 20 ml of demi water under mechanical stirring for 1 h. The pH was adjusted to 4.5 using 25% HCl. The mixture was crosslinked with 1.4 mol % of BDDE (1.4-butanediol diglycidyl ether) (78 µl) at 50° C. for 18 hours. The gel was chopped and the pieces were dried in a fluidised bed drier for 30 minutes at 100° C. The dried gel was ground and washed with excess demi water on a 80 µm sieve to remove any salts present. Then the gel was dried in the fluidised bed drier at 80° C. for 1 hour. The material was characterised in synthetic urine with the following results: 93% TOS/7% CMC: FSC: 26 g/g, CRC: 15.5 g/g, AUL: 19 g/g, pH gel 4.9.

EXAMPLE 9

Absorbent 6-carboxy Starch Crosslinked Under Acidic Conditions

Five g of TEMPO-oxidised starch (TOS, degree of oxidation 0.70) was dissolved in 20 ml of demi water under mechanical stirring for 1 h. The pH was adjusted to 4.5 using 25% HCl. The mixture was crosslinked with 2.0 mol % of BDDE (113 µl) at 50° C. for 18 hours. The gel was chopped and the pieces were dried in a fluidised bed drier for 30 minutes at 100° C. The dried gel was ground and washed with excess demi water on a 80 µm sieve to remove any salts present. Then the gel was dried in the fluidised bed drier at 80° C. for 1 hour. The material was characterised in synthetic urine with the following results: 100% TOS: FSC: 27 g/g, CRC: 16 g/g, AUL: 19 g/g, pH gel 4.8.

EXAMPLE 10

Crosslinking of 6-carboxy Starch by Extrusion

In an extruder, 50 grams of 6-carboxy starch (0.25 mol) is mixed with 50 ml of a 0.3 M HCl solution containing 30 µl butanediol diglycidyl ether (0.15 mmol). The paste is then extruded at 150° C. with an average residence time of 1 minute in the extruder. At the extrusion die the crosslinked polysaccharide is chopped into small pieces. The small pieces of gel are then dried in a fluidised bed drier for 30 minutes at 100° C. The dried particles are ground and sieved to obtain a final particle size of 100–800 µm. The absorption properties are comparable to those of the superabsorbent polysaccharide crosslinked in a conventional way.

EXAMPLE 11

Absorbent 6-carboxy Starch/CMC Crosslinked Under Acidic Conditions

Three batches of 4 g of desalted TEMPO-oxidised starch (TOS, degree of oxidation 0.70) were dissolved in demi water to obtain 20 wt %, 40 wt % and 50 wt % TOS solutions, respectively. The pH of the solutions was about 4.6. To the solutions 0.124 g of CMC (Cekol 50,000, degree of substitution 0.8) was added, followed by thorough mixing. The mixtures were crosslinked at 50° C. for 18 hours, with 1.4, 0.7, and 0.5 mol % of BDDE, respectively. Gels obtained were sized and, subsequently, dried in a fluidised bed drier for 1 hour at 100° C. The dried gels were ground and re-swollen in an excess of demi water. By addition of 2 M HCl, pH of the gel was adjusted to pH of 4.7–4.8 in demi water. Subsequently, the re-swollen gels were washed with excess demi water on a 80 µm sieve to remove salts present. Then the gels were dried in the fluidised bed drier at 100° C. for 1 hour. The materials were characterised in synthetic urine with the following results for the 40% TOS material: DXL (=degree of crosslinking in mol % BDDE): 0.7; FSC: 26.5 g/g; CRC: 15.5 g/g; AUL 14 g/g pH gel: 4.2. Comparable results were obtained when using 20% or 50% TOS solutions, instead of 40%.

EXAMPLE 12

Absorbent 6-carboxy Starch Crosslinked Under Acidic Conditions

Three batches of 4 g of desalted TEMPO-oxidised starch (TOS, degree of oxidation 0.70) were dissolved in demi water to obtain 20 wt %, 40 wt % and 50 wt % TOS solutions, respectively. The pH of the solutions was about 4.6. The solutions were cross-linked at 50° C. for 18 hours, with 2.0, 0.75, and 0.6 mol % of BDDE, respectively. Gels obtained were sized and, subsequently, dried in a fluidised bed drier for 1 hour at 100° C. The dried gels were ground and re-swollen in an excess of demi water. By addition of 2 M HCl, pH of the gel was adjusted to pH of 4.7–4.8 in demi water. Subsequently, the re-swollen gels were washed with excess demi water on a 80 µm sieve to remove salts present. Then the gels were dried in the fluidised bed drier at 100° C. for 1 hour. The materials were characterised in synthetic urine with the following results for the 40% TOS material: DXL 0.75; FSC: 28 g/g; CRC: 15 g/g; AUL 14 g/g; pH gel: 4.1. Comparable results were obtained when using 20% or 50% TOS solutions instead of 40%.

EXAMPLE 13

Absorbent 6-carboxy Starch/CMC Crosslinked Under Acidic Conditions

Three batches of 4 g of desalted TEMPO-oxidised starch (TOS, degree of oxidation 0.70) were dissolved in demi water to obtain 40 wt % TOS-solutions. The pH of solutions was about 4.6. To each solution 0.124 g of CMC (Cekol 50,000, degree of substitution 0.8) was added, and the whole was mixed thoroughly. Mixtures were cross-linked with 0.7 mol % of BDDE at 50° C. for 18 hours, 70° C. for 2.5 hours, and 100° C. for 1 hour, respectively. Gels obtained were sized and, subsequently, dried in a fluidised bed drier for 1 hour at 100° C. The dried gels were ground and re-swollen in an excess of demi water. By addition of 2 M HCl, pH of the gel was adjusted to pH of 4.7–4.8 in demi water. Subsequently, the re-swollen gels were washed with excess demi water on a 80 µm sieve to remove any salts present. Then the gels were dried in the fluidised bed drier at 100° C. for 1 hour. The materials were characterised in synthetic urine with the following results:

| XL, temp. (° C.) | XL time (h) | FSC (g/g) | CRC (g/g) | AUL (g/g) | pH gel |
|---|---|---|---|---|---|
| 50 | 18 | 26.5 | 15.5 | 14 | 4.2 |
| 70 | 2.5 | 27 | 14 | 13 | 3.8 |
| 100 | 1 | 27 | 15.5 | 11.5 | 3.9 |

EXAMPLE 14

Absorbent 6-carboxy Starch Crosslinked Under Acidic Conditions

Fifty g of desalted freeze-dried TEMPO-oxidised starch (TOS, degree of oxidation 0.70) was kneaded till a fibrous structure was obtained, and subsequently demi water (21.4 ml of demi water) was added. The whole was kneaded for 3 minutes at 17° C. to obtain 70 wt % TOS paste (pH of paste was ca. 4.6). To this paste 0.4 mol % BDDE was added and the whole was again kneaded for 3.5 minutes at 17° C. Then the paste was crosslinked for 16 hours at 50° C. The gel obtained was sized and dried in a fluidised bed drier for 1 hour at 80° C. Dried gel particles were re-swollen in 10 liters of demi water, and subsequently dried in the fluidised bed drier for 1.5 hours at 80° C. The material was characterised in synthetic urine with the following results: FSC: 27 g/g, CRC: 14.5 g/g, AUL: 17.5 g/g, pH gel 4.9.

What is claimed is:

1. A process of producing a superabsorbent polysaccharide derivative, comprising the sequential steps of:
   (a) crosslinking at least one polysaccharide containing acidic groups with a crosslinking agent to produce a gel;
   (b) ensuring that the pH of the polysaccharide is between 3.5 and 5.5;
   (c) comminuting the acidified polysaccharide gel; and
   (d) drying the comminuted polysaccharide at elevated temperature.

2. A process according to claim 1, in which the polysaccharide containing acidic groups comprises carboxymethylcellulose, further comprising the step of contacting the crosslinked polysaccharide with an organic solvent which is at least partly miscible with water, between step (b) and step (c).

3. A process according to claim 2, in which said organic solvent is a lower alcohol, a water-miscible ketone or a water-miscible ether.

4. A process according to claim 1, in which the polysaccharide containing acidic groups is a carboxymethyl polysaccharide further containing carboxyl groups resulting from oxidation of saccharidic hydroxymethyl or hydroxymethylene groups, or phosphonic or sulphonic acid groups.

5. A process according to claim 1, in which the polysaccharide containing acidic groups comprises a 6-carboxy polysaccharide.

6. A process according to claim 1 in which the polysaccharide containing acidic groups contains 0.3–3.0 carboxyl groups per monosaccharide unit.

7. A process according to claim 1, in which said crosslinking agent is a bis-epoxy compound, and the polysaccharide is acidified before step (a).

8. A process according to claim 1, in which said crosslinking step is performed at a temperature of at least 100° C. and/or at a concentration of the polysaccharide of between 25 and 75% by weight.

9. A process according to claim 8, in which a plasticizer is used during said crosslinking step.

10. A process according to claim 1, in which said drying step (d) is performed using a fluidized bed, at a temperature of between 50 and 130° C.

11. A process according to claim 1, in which said drying step (d) is followed by a heat treatment at a temperature of between 80 and 150° C.

12. A process according to claim 1, in which an additional surface-crosslinking step is performed after step (c) or after step (d).

13. A process according to claim 2, in which said organic solvent is methanol or ethanol.

14. A process according to claim 5, in which the polysaccharide containing acidic groups comprises 6-carboxy starch.

15. A process according to claim 5, in which the polysaccharide containing acidic groups comprises a 6-carboxy polysaccharide mixed with a carboxyalkylated polysaccharide.

16. A process according to claim 1, in which said crosslinking step is performed at a temperature of between 120 and 180° C.

17. A process according to claim 9, in which glycerol is used as a plasticizer.

* * * * *